(12) United States Patent
Choi et al.

(10) Patent No.: US 9,518,290 B2
(45) Date of Patent: Dec. 13, 2016

(54) METHOD FOR DETECTING NUCLEIC ACIDS BY AMPLIFICATION OF A CIRCULARIZED NUCLEIC ACID

(71) Applicant: Samsung Electronics Co., Ltd., Suwon-si, Gyeonggi-do (KR)

(72) Inventors: Ko-bong Choi, Osan-si (KR); Sea-hee Kim, Seoul (KR); Joon-ho Kim, Seongnam-si (KR); Joo-won Rhee, Yongin-si (KR); Sunok Jung, Seongnam-si (KR); Kyu-youn Hwang, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 301 days.

(21) Appl. No.: 14/251,814

(22) Filed: Apr. 14, 2014

(65) Prior Publication Data

US 2015/0072882 A1   Mar. 12, 2015

(30) Foreign Application Priority Data

Sep. 10, 2013  (KR) .......................... 10-2013-0108627

(51) Int. Cl.
*C12Q 1/68* (2006.01)

(52) U.S. Cl.
CPC ........... *C12Q 1/6844* (2013.01); *C12Q 1/6816* (2013.01)

(58) Field of Classification Search
None
See application file for complete search history.

(56) References Cited

U.S. PATENT DOCUMENTS

| 7,618,776 B2 | 11/2009 | Lizardi |
| 8,053,188 B2 | 11/2011 | Gullberg et al. |
| 2002/0182598 A1* | 12/2002 | Zhang .................... C12Q 1/682 435/6.1 |
| 2012/0021930 A1 | 1/2012 | Schoen et al. |

FOREIGN PATENT DOCUMENTS

JP    2002-315575 A    10/2002

OTHER PUBLICATIONS

Larsson et al., In situ genotyping individual DNA molecules by target-primed rolling-circle amplification of padlock probes, *Nature Methods*, 1(3): 227-232 (2004).
Schouten et al., Relative quantification of 40 nucleic acid sequences by multiplex ligation-dependent probe amplification, *Nucleic Acids Research*, 30(12): e57 pp. 2-13 (2002).
Shen et al., High-quality DNA sequence capture of 524 disease candidate genes, *PNAS*, 108(16): 6549-6554 (2011).
Turner et al., Massively parallel exon capture and library-free resequencing across 16 individuals, *Nat. Methods*, 6(5): 315-316 (2009).
Van Doorn et al., Robust Detection and Identification of Multiple Oomycetes and Fungi in Environmental Samples by Using a Novel Cleavable Padlock Probe-Based Ligation Detection Assay, *Appl. and Environ. Microbiol.*; 75(12): 4185-4193 (2009).

\* cited by examiner

*Primary Examiner* — Angela M Bertagna
(74) *Attorney, Agent, or Firm* — Leydig, Voit & Mayer, Ltd.

(57) ABSTRACT

A method of detecting a target nucleic acid, and a polynucleotide and a composition for detecting a target nucleic acid.

15 Claims, 4 Drawing Sheets

SEQUENCE LISTING

<160> NUMBER OF SEQ ID NOS: 4

<210> SEQ ID NO 1
<211> LENGTH: 86
<212> TYPE: DNA
<213> ORGANISM: Artificial Sequence -continued

```
<220> FEATURE:
<223> OTHER INFORMATION: Synthetic (padlock probe)

<400> SEQUENCE: 1
atcgtccacc gcaaatgcga tgggatttcc attgatgaca ttcccgttct cagccttgac      60
ggtgccagca gatgtggatc agcaag                                          86

<210> SEQ ID NO 2
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 2
gatgggattt ccattgatga ca                                              22

<210> SEQ ID NO 3
<211> LENGTH: 19
<212> TYPE: DNA
<213> ORGANISM: Artificial Sequence
<220> FEATURE:
<223> OTHER INFORMATION: Synthetic (reverse primer)

<400> SEQUENCE: 3
cggactcgtc atactcctg                                                  19

<210> SEQ ID NO 4
<211> LENGTH: 22
<212> TYPE: DNA
<213> ORGANISM: Artificial Sequence
<220> FEATURE:
<223> OTHER INFORMATION: Synthetic (Taqman probe)

<400> SEQUENCE: 4
ccgttctcag ccttgacggt gc                                              22
```

METHOD FOR DETECTING NUCLEIC ACIDS BY AMPLIFICATION OF A CIRCULARIZED NUCLEIC ACID

RELATED APPLICATION

This application claims the benefit of Korean Patent Application No. 10-2013-00108627, filed on Sep. 10, 2013, in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 1,106 bytes ASCII (Text) file named "715884_ST25.TXT," created Apr. 11, 2014.

BACKGROUND

1. Field

The present disclosure relates to methods of detecting target nucleic acids, and polynucleotides and compositions used for detecting target nucleic acids.

2. Description of the Related Art

Real-time polymerase chain reaction (RT-PCR) is a method used to monitor a process of amplification in real time whereby PCR products are amplified exponentially, and is one of the most commonly used methods in molecular biology. In particular, RT-PCR is used to monitor a process of producing PCR amplification products in real-time, to thereby quantify an amount of DNA in an original sample using an apparatus in which a thermal cycler and a fluorophotometer are integrated as one body.

The RT-PCR method may be divided into an absolute quantification analysis and a relative quantification analysis. The absolute quantification analysis is used to quantify the amount of DNA in a sample. After simultaneously performing qRT-PCR for a standard sample and an unknown sample, a standard curve may be generated from the standard sample. The amount of target DNA in the unknown sample can then be quantified from the standard curve. Generally, the standard curve (x-axis: $Log_{10}$ (standard sample); y-axis: the number of cycle threshold) of the standard sample is ideal when a correlation index ($R^2$) is about 1. Ideally, a slope derived from the standard curve is about −3.3 for a $\frac{1}{10}\times$ diluted PCR product, and a slope is about −2.33 for a $\frac{1}{5}\times$ diluted PCR product.

Currently, in most cases when a qRT-PCR is performed by a fluorescence method using probes such as Taqman™, a relatively short region of DNA is used as a target nucleic acid to maintain precise levels of nucleic acid quantification and detection. More time is needed for the elongation of longer target nucleic acids, however, and thus the detection and quantification of longer target nucleic acids of interest are less precise.

Accordingly, there is still a need for a method of detecting and quantifying long target nucleic acids with excellent precision and sensitivity, including instances when a conventional method such as RT-PCR are used.

SUMMARY

Provided is a method of detecting a target nucleic acid, the method comprising:
incubating a first polynucleotide and a sample comprising a target nucleic acid, whereby the target nucleic acid and the first polynucleotide hybridize to form a hybridization product,
wherein the first polynucleotide comprises a first complementary region that is complementary to at least two continuous nucleotides of a first region of the target nucleic acid; and a second complementary region that is complementary to at least two continuous nucleotides of a second region of the target nucleic acid, wherein the second region of the target nucleic acid is located 3' of (i.e., downstream from) the first region of the target nucleic acid;
incubating the hybridization product in the presence of a first nucleic acid polymerase to extend the first polynucleotide to prepare an extended product;
incubating the extended product in the presence of a nucleic acid ligase to prepare a second polynucleotide having a cyclic structure;
incubating the second polynucleotide having a cyclic structure in the presence of a primer set and a second nucleic acid polymerase to amplify the second polynucleotide having a cyclic structure to prepare an amplification product,
wherein the primer set comprises
a forward primer comprising a polynucleotide sequence that is identical to at least two continuous nucleotides of a third region of the first polynucleotide located between the first and second complementary regions of the first polynucleotide, and a reverse primer comprising a polynucleotide sequence that is identical to at least two continuous nucleotides located between the first and second regions of the target nucleic acid, or
a forward primer comprising a polynucleotide sequence that is identical to at least two continuous nucleotides located between the first and second regions of the target nucleic acid, and a reverse primer comprising a polynucleotide sequence that is identical to at least two continuous nucleotides located between the first and second complementary regions of the first polynucleotide; and
detecting the amplification product to detect the target nucleic acid.

Additionally, provided are polynucleotides comprising a first complementary region that is complementary to at least two continuous nucleotides of a first region of a target nucleic acid; a second complementary region that is complementary to at least two continuous nucleotides of a second region of the target nucleic acid, wherein the second region of the target nucleic acid is located 3' (downstream) from the first region of the target nucleic acid; and a third region that is located 5' (upstream) from the second complementary region, and is identical or complementary to at least two continuous nucleotides of a forward primer or a reverse primer, as well as kits and compositions comprising the polynucleotide and target and primer sequences.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. As used herein "downstream" means in the 3' direction, i.e., in the direction of the 3' terminus of a polynucleotide, and "upstream" means in the 5' direction, i.e., in the direction of the 5' terminus of a polynucleotide than a first nucleic acid.

Provided is a method of detecting a target nucleic acid, the method comprising:

incubating a first polynucleotide and a sample comprising a target nucleic acid, whereby the target nucleic acid and the first polynucleotide hybridize to form a hybridization product, wherein the first polynucleotide comprises a first complementary region that is complementary to at least two continuous nucleotides of a first region of the target nucleic acid; and a second complementary region that is complementary to at least two continuous nucleotides of a second region of the target nucleic acid, wherein the second region of the target nucleic acid is located downstream from the first region of the target nucleic acid;

incubating the hybridization product in the presence of a first nucleic acid polymerase to extend the first polynucleotide to prepare an extended product;

incubating the extended product in the presence of a nucleic acid ligase to prepare a second polynucleotide having a cyclic structure;

incubating the second polynucleotide having a cyclic structure in the presence of a primer set and a second nucleic acid polymerase to amplify the second polynucleotide having a cyclic structure to prepare an amplification product, wherein the primer set is a first primer set comprising a forward primer comprising a polynucleotide sequence that is identical to at least two continuous nucleotides of a third region of the first polynucleotide located downstream from the first complementary region of the target nucleic acid and upstream from the second complementary region of the first polynucleotide, and a reverse primer comprising a polynucleotide sequence that is identical to at least two continuous nucleotides located downstream from the first region of the target nucleic acid and upstream from the second region of the target nucleic acid, or a second primer set comprising a forward primer including a polynucleotide sequence that is identical to at least two continuous nucleotides located downstream from the first region of the target nucleic acid and upstream from the second region of the target nucleic acid, and a reverse primer comprising a polynucleotide sequence that is identical to at least two continuous nucleotides located downstream from the first complementary region of the first polynucleotide and upstream from the second complementary region of the first polynucleotide; and detecting the amplification product to detect the target nucleic acid.

The sample may comprise a biological sample or DNA, RNA, or a fragment thereof separated from the biological sample. The sample may include a virus or a biological derivative. For example, the sample may include at least one selected from the group consisting of blood, saliva, urine, feces, a tissue, a cell, and a biopsy product. The sample may include a stored biological sample or DNA or RNA separated therefrom. The sample may be stored according to a storage method known in the art. The sample may be stored for one year or longer, for example, for about one year to about 10 years. The DNA or RNA may be DNA or RNA derived from a refrigerated tissue sample or a formalin-fixed paraffin-embedded tissue sample stored at room temperature. Methods of separating DNA or RNA from a biological sample are known in the art.

As used herein "target nucleic acid" refers to a nucleic acid to be detected. The target nucleic acid may be a genomic DNA, a genomic RNA, or a complementary DNA (cDNA). "Genome" as used herein refers to the full complement of genetic material within an organism, and includes genes and non-coding sequences. "Genomic DNA" as used herein refers to a genome consisting of DNAs. "Genomic RNA" as used herein refers to a genome consisting of RNAs. The term "cDNA" as used herein refers to a DNA synthesized from a messenger RNA (mRNA) catalyzed by a reverse transcriptase.

The target nucleic acid has a first and second region that hybridize to the first and second complementary regions of the first polynucleotide. The first and second regions of the target nucleic acid and, thus, the first and second complementary regions of the first polynucleotide, can have any suitable length (number of nucleotides (nts)) sufficient to allow the first and second regions of the target nucleic acid to hybridize to the first and second complementary regions of the first polynucleotide, respectively. For example, the first and second regions of the target nucleic acid, and the first and second complementary regions of the first polynucleotide may have about 2 or more nts, such as about 5 or more nts (e.g., about 5 to 50 nts, or about 5 to 20 nts, or 5 to 15 nts).

The first region and the second region of the target nucleic acid may be separated by any suitable number of nucleotides, such as about 18 nucleotides to about 10000 nucleotides. For example, first region and the second region of the target nucleic acid may be separated by about 18 nts to about 9000 nts, about 18 nts to about 8000 nts, about 18 nts to about 7000 nts, about 17 nts to about 6000 nts, about 18 nts to about 5000 nts, about 18 nts to about 4000 nts, about 18 nts to about 3000 nts, about 18 nts to about 2000 nts, about 18 nts to about 1000 nts, about 18 nts to about 900 nts, about 18 nts to about 800 nts, about 18 nts to about 700 nts, about 18 nts to about 600 nts, about 18 nts to about 500 nts, about 18 nts to about 400 nts, about 18 nts to about 300 nts, about 18 nts to about 200 nts, or about 18 nts to about 100 nts.

Similarly, the first and second complementary regions of the first polynucleotide may be separated by any suitable number of nucleotides, such as about 18 nucleotides to about 500 nucleotides. For example, first and second complementary regions of the first polynucleotide may be separated by about 18 nucleotides to about 300 nucleotides.

Although the first and second complementary regions of the first polynucleotide hybridize to the first and second regions of the target nucleic acid, respectively, the sequence of the first polynucleotide separating the first and second complementary regions desirably does not hybridize to any part of the sequence of the target nucleic acid. This allows the portion of the first polynucleotide between the first and second complementary regions to form a free "loop" when the first and second complementary regions are hybridized to the target.

The length of the first polynucleotide may be about 30 nts to about 200 nts, about 35 nts to about 190 nts, about 40 nts to about 180 nts, about 45 nts to about 170 nts, about 50 nts to about 160 nts, about 55 nts to about 150 nts, about 60 nts to about 140 nts, about 65 nts to about 130 nts, about 70 nts to about 120 nts, about 75 nts to about 110 nts, or about 80 nts to about 100 nts. The first polynucleotide may include DNA, RNA, peptide nucleic acid (PNA), locked nucleic acid (LNA), a nucleotide analog, or any combination thereof.

The hybridization of polynucleotides and target nucleic acids may be performed by a method known in the art. For example, the method may include incubating a sample including the first polynucleotide and a sample including the target nucleic acid in a buffer known to be suitable for nucleic acid hybridization. A suitable temperature for hybridization may be, for example, about 0° C. to about 65° C., about 10° C. to about 60° C., about 20° C. to about 55° C., about 25° C. to about 50° C., or about 30° C. to about 45° C. The temperature may be suitably selected according to the sample including target nucleic acid and a length of the first polynucleotide sequence. A suitable period of time for hybridization may be, for example, about 1 hour to about 12 hours (overnight).

The first nucleic acid polymerase may comprise a DNA polymerase. The DNA polymerase may comprise a T4 DNA polymerase, a T7 polymerase, a Klenow fragment, a DNA polymerase I, a Taq DNA polymerase, a Bst DNA polymerase (exonuclease minus), a pyrophage 3173 DNA polymerase, a Tth DNA polymerase, a Pfx DNA polymerase, a Tfi DNA polymerase, a Tfl DNA polymerase, a hot start polymerase, a BcaBEST DNA polymerase, or any combination thereof.

The extending of the first polynucleotide refers to extending a 3' terminus of the first polynucleotide in a template-dependent manner. The extending may be performed by incubating the first polynucleotide in the presence of a nucleic acid polymerase. The incubating may be performed at a suitable temperature for activity of the nucleic acid polymerase, for example, about 20° C. to about 70° C., about 25° C. to about 60° C., about 30° C. to about 50° C., or about 30° C. to about 40° C. A suitable period of time for the incubating may be about 10 minutes to about 12 hours (overnight), or about 30 minutes to about 12 hours (overnight).

The nucleic acid ligase may comprise a DNA ligase. The DNA ligase may comprise a T4 DNA ligase, a T3 DNA ligase, a T7 DNA ligase, an *Escherichia coli* DNA ligase, an Ampligase DNA ligase, a CIRCLIGASE™ ssDNA ligase, or any combination thereof.

The second polynucleotide having a cyclic structure may be formed by incubating the first nucleotide in the presence of the nucleic acid ligase. A suitable temperature for the incubating may be a suitable temperature for activity of the nucleic acid ligase, for example, about 0° C. to about 50° C., about 5° C. to about 40° C., about 10° C. to about 35° C., or about 15° C. to about 30° C. A suitable period of time for the incubating may be, for example about 10 minutes to about 12 hours (overnight), or about 30 minutes to about 12 hours (overnight).

The term "primer" as used herein refers to a short strand of nucleic acid that acts as a starting point for a template-dependent nucleic acid synthesis. The primer refers to a polynucleotide sequence complementary to a 3' terminus of any one of sense strand or an anti-sense strand of the target nucleic acid. "Sense strand" as used herein refers to a target nucleic acid strand. For example, the sense strand may be a nucleic acid strand having the same sequence as an mRNA. The anti-sense strand refers to a strand complementary to the sense strand. For example, the anti-sense strand may be a template for an mRNA synthesis.

"Primer set" as used herein refers to a set comprising a forward primer and a reverse primer. The primer set may comprise, for example, a first primer set comprising a forward primer including a polynucleotide sequence that is identical to at least two continuous nucleotides of a third region of the first polynucleotide located downstream from the first complementary region of the first polynucleotide and upstream from the second complementary region of the first polynucleotide, and a reverse primer comprising a polynucleotide sequence that is identical to at least two continuous nucleotides located downstream from the first region of the target nucleic acid and upstream from the second region of the target nucleic acid; or a second primer set comprising a forward primer comprising a polynucleotide sequence that is identical to at least two continuous nucleotides located downstream from the first region of the target nucleic acid and upstream from the second region of the target nucleic acid, and a reverse primer comprising a polynucleotide sequence that is identical to at least two continuous nucleotides located downstream from the first complementary region of the first polynucleotide and upstream from the second complementary region of the first polynucleotide.

The length of the primer in the primer set may be, for example, about 5 nts to about 30 nts, about 7 nts to about 30 nts, about 9 nts to about 30 nts, about 12 nts to about 30 nts, about 15 nts to about 30 nts, about 17 nts to about 27 nts, or about 20 nts to about 27 nts.

The second nucleic acid polymerase may be a DNA polymerase. The DNA polymerase may be a T4 DNA polymerase, a T7 polymerase, a Klenow fragment, a DNA polymerase I, a Taq DNA polymerase, a Bst DNA polymerase (exonuclease minus), a pyrophage 3173 DNA polymerase, a Tth DNA polymerase, a Pfx DNA polymerase, a Tfi DNA polymerase, a Tfl DNA polymerase, a hot start polymerase, a BcaBEST DNA polymerase, or any combination thereof.

The term "amplification" as used herein refers to increasing a number of nucleic acid copies and producing DNA from RNA. The amplification may be performed by using a method known in the art. An amplification method may include a thermal cycling (that is, a thermal cycling amplification) or may be performed isothermally (that is, an isothermal amplification). The amplification method may include a polymerase chain reaction (PCR), a nucleic acid sequence-based amplification (NASBA), a ligase chain reaction (LCR), a strand displacement amplification (SDA), a multiple displacement amplification (MDA), a rolling circle amplification (RCA), or any combination thereof. The "PCR" may be a method that includes amplification of the target nucleic acid from a primer set that specifically binds to the target nucleic acid, by using a polymerase. For example, the nucleic acid amplification includes repeating denaturation, annealing, and elongation. The term "annealing" as used herein may be used interchangeably with "hybridization". The amplification may be, for example, real-time nucleic acid amplification. The term "real-time nucleic acid amplification (RT-PCR)" as used herein is a method of observing increasing PCR products in each PCR cycle in real-time, and the method includes detecting and quantitatively analyzing a fluorescent material (e.g., a fluorophore) that reacts with the PCR product of a sample.

The amplification of the second polynucleotide having a cyclic structure may be performed in the presence of a probe. The probe may include a polynucleotide sequence that is identical or complementary to at least two continuous nucleotides of a third region located downstream from the first complementary region and upstream from the second complementary region of the first polynucleotide. The probe may hybridize to an amplification product of the second polynucleotide. The probe may, for example, include a polynucleotide sequence identical or complementary to at least two nucleotides downstream from the first complementary region, downstream from the third region, and upstream from the second complementary region of the first polynucleotide. The probe may, for example, include a polynucleotide sequence identical or complementary to at least two nucleotides downstream from the first complementary region and upstream from the third region of the first polynucleotide.

The probe may be labeled with a fluorescence resonance energy transfer (FRET) set. The probe may be, for example, a probe in which a 5' end thereof is labeled by at least one fluorescence marker selected from the group consisting of 6-carboxyfluorescein (FAM), VIC, tetrachlorofluorescein (TET), JOE, HEX, CY3, CY5, ROX, RED610, TEXAS RED, RED670, and NED, or a 3' end thereof is labeled by at least one fluorescent quencher selected from the group consisting of 6-tetramethylrhodamine (TAMRA), BHQ-1,2, 3, and a molecular groove binding non-fluorescence quencher (MGBNFQ).

The detection of the amplification product may include hybridizing the probe and the amplification product to detect a probe signal.

The detection of the amplification product may be performed in real-time.

The detection of the amplification product may comprise detecting a zone improvement plan (zip)-code sequence comprising a polynucleotide sequence identical or complementary to at least two continuous nucleotides located downstream from the first complementary region of the first polynucleotide or upstream from the second complementary region of the first polynucleotide. For example, the detection of the amplification product may be detecting a zip-code sequence including a polynucleotide sequence identical to at least two continuous nucleotides located downstream from the first complementary region, downstream from the third region, and upstream from the second complementary region. For example, the detection of the amplification product may be detecting a zip-code sequence including a polynucleotide sequence identical to at least two continuous nucleotides located downstream from the first complementary region and upstream from the third region of the first polynucleotide. The detection of the zip-code sequence may be performed by using a zip-code microarray. The detection of the zip-code sequence may include hybridizing the zip-code sequence and a polynucleotide sequence in which at least two nucleotides are complementary to the zip-code sequence, wherein the polynucleotide sequence is bound to a solid support.

The method described above may further include quantifying a detected target nucleic acid.

Additionally, provided is a polynucleotide comprising a first complementary region that is complementary to at least two continuous nucleotides of a first region of the target nucleic acid;

a second complementary region that is complementary to at least two continuous nucleotides of the second region of the target nucleic acid, wherein the second region of the target nucleic acid is located downstream from the first region of the target nucleic acid, and the first region of the target nucleic acid is complementary to the first complementary region; and a third region that is located downstream from the first complementary region and upstream from the second complementary region, and is identical or complementary to at least two continuous nucleotides of a forward primer or a reverse primer.

The target nucleic acid, the first complementary region, the second complementary region, the forward primer, the reverse primer, and the third region are as described above.

The length of the polynucleotide may be about 30 nts to about 200 nts, about 35 nts to about 190 nts, about 40 nts to about 180 nts, about 45 nts to about 170 nts, about 50 nts to about 160 nts, about 55 nts to about 150 nts, about 60 nts to about 140 nts, about 65 nts to about 130 nts, about 70 nts to about 120 nts, about 75 nts to about 110 nts, or about 80 nts to about 100 nts. The polynucleotide may comprise DNA, RNA, PNA, LNA, a nucleotide analog, or any combination thereof.

The polynucleotide may comprise a polynucleotide sequence that is identical to at least two continuous nucleotides of the probe. The polynucleotide may further comprise a linker, a zip-code sequence, a restriction enzyme recognition site, or any combination thereof. The linker may be a polynucleotide sequence that does not hybridize to the target nucleic acid. A length of the linker may be about 5 nts to about 200 nts, about 10 nts to about 190 nts, about 20 nts to about 180 nts, about 45 nts to about 170 nts, about 50 nts to about 160 nts, about 55 nts to about 150 nts, about 60 nts to about 140 nts, about 65 nts to about 130 nts, about 70 nts to about 120 nts, about 75 nts to about 110 nts, or about 80 nts to about 100 nts.

The zip-code sequence may be a polynucleotide sequence formed of 6 tetramers from a 5' terminus. The polynucleotide sequence that may be hybridized to the zip-code sequence may be bound to a solid support. The solid support may be a microarray substrate.

As used herein "restriction enzyme recognition site" refers to a region that is recognized and cut by a restriction enzyme. The restriction enzyme recognition site may comprise any suitable site.

Additionally, provided is a composition or a kit, for detecting a target nucleic acid. The composition or kit comprises a polynucleotide and a nucleic acid polymerase, wherein the polynucleotide includes a first complementary region that is complementary to at least two continuous nucleotides of a first region of a target nucleic acid, a second complementary region that is complementary to at least two continuous nucleotides of a second region of the target nucleic acid, wherein the second region of the target nucleic acid is located downstream from the first region of the target nucleic acid, and a third region that is located downstream from the first complementary region and upstream from the second complementary region and is identical or complementary to at least two continuous nucleotides of a forward primer or a reverse primer.

The polynucleotide, the first complementary region, the second complementary region, the forward primer, the reverse primer, the third region, the nucleic acid polymerase, the target nucleic acid, and the detection are as described above.

The composition for detecting the target nucleic acid may further comprise a material known for amplification of the nucleic acid. For example, the composition may further include a buffer, a cofactor, and/or a substrate, which are needed for the activity of the nucleic acid polymerase.

The kit for detecting the target nucleic acid may further include a material needed for the amplification of nucleic acids known in the art. For example, the kit may further comprise a buffer, a cofactor, and/or a substrate, which are needed for the activity of the nucleic acid polymerase. The kit may further include a manual that may be used to amplify the nucleic acid.

When the target nucleic acid is detected by using the polynucleotide, a short region of the polynucleotide sequence may be amplified and thus, a long target nucleic acid may be detected and quantified with high sensitivity and precision.

Exemplary polynucleotides for use in the methods, polynucleotides, compositions, and kits described herein may comprise, but are not limited to the polynucleotides illustrated in FIGS. 1A through 1D, wherein: 1a is a polynucleotide sequence of a probe complementary to a portion of the 5' terminal region of a target nucleic acid (a first complementary region); 1b is a portion of the 5' terminal region of the target nucleic acid (a first region) complimentary to 1a of the probe; 2a is a polynucleotide sequence of a probe complementary to a portion of the 3' terminal region of the target nucleic acid (a second complementary region); 2b is a portion of the 3' terminal region of the target nucleic acid complimentary to 2a; 3 is a forward primer sequence (a third region); 4 is a probe sequence; 5 is a reverse primer sequence; 6 is a reverse primer sequence (a third region); and 7 is a forward primer sequence.

The present invention will be described in further detail with reference to the following examples. These examples are for illustrative purposes only and are not intended to limit the scope of the present invention.

Example 1

Preparing a Padlock Probe

To amplify a human β-actin gene, Bioneer Corp was requested to prepare a padlock probe having the following polynucleotide sequence:

Padlock probe:
(SEQ ID NO: 1)
5'-ATCGTCCACCGCAAATGC<u>GATGGGATTTCCATTGATGACA</u>TTCCC
*GTTCTCAGCCTTGACGGTGC*CAGCAGATGTGGATCAGCAAG-3'

Bolded letters in the polynucleotide sequence of SEQ ID NO: 1 indicate a sequence complementary to nucleotides 1206 to 1224 and 1158 to 1179 from the 5' terminus of a human β-actin gene (GenBank Accession No. NM_001101.3) (each of which is a first complementary region and a second complementary region), the underlined letters indicate a sequence identical to a polynucleotide sequence of a forward primer (a third region), and the italicized letters indicate a sequence identical to a polynucleotide sequence of a TAQMAN™ probe (a fourth region).

Example 2

Preparing Cyclic DNA by Using a Padlock Probe

The padlock probe prepared in Example 1 was hybridized to human genomic DNA to prepare a hybridized product, and the hybridized product was elongated and ligated to prepare cyclic DNA.

8 ng, 40 ng, 200 ng, or 1000 ng of human genomic DNA (Cat. No. G3041 available from Promega) and 100 ng of the padlock probe prepared in Example 1 were incubated in the presence of a 1× reaction buffer (50 mM of NaCl, 10 mM of Tris-HCl, 10 mM of $MgCl_2$, 1 mM of DTT, 0.25 mM of dNTP, and pH 7.9) at a temperature of 95° C. for 5 minutes to prepare an incubated reaction product. 3 units of T4 DNA polymerase (Cat. No. M0203S available from NEB) were added to the incubated reaction product, and then incubated at a temperature of 37° C. for 30 minutes to prepare a reaction product. The reaction product was incubated at a temperature of 70° C. for 20 minutes to inactivate the T4 DNA polymerase.

Then, 400 units of T4 DNA polymerase (Cat. No. M0202S available from NEB) and 1 mM of ATP were added to the reaction product and the reaction product was incubated at a temperature of 20° C. for 30 minutes.

Example 3

Quantitative Real Time-Polymerase Chain Reaction (qRT-PCR) of Human β-Actin Gene qRT-PCR was performed on the product obtained from Example 2 with primers and probes illustrated in Table 1, below.

TABLE 1

| | Nucleotide sequence | |
|---|---|---|
| Forward primer | 5'-GATGGGATTTCCATTGATGACA-3' | SEQ ID NO: 2) |

TABLE 1-continued

| | Nucleotide sequence | |
|---|---|---|
| Reverse primer | 5'-CGGACTCGTCATACTCCTG-3' | (SEQ ID NO: 3) |
| TaqMan™ probe | 5'-FAM-CCGTTCTCAGCCTTGACGGTGC-BHQ1-3' | (SEQ ID NO: 4) |

5 µl of the product obtained from Example 2 (⅕× diluted), 10 µM of the forward primer, 10 µM of the reverse primer, 20 µM of the TAQMAN™ probe, 10 µl of LIGHTCY-CLER® 480 Probes Master (available from Roche), and water were mixed to prepare a final volume of 20 µl of a reaction mixture.

The qRT-PCR was performed at a temperature of 95° C. for 10 seconds and at 55° C. for 30 seconds for one cycle, and the cycle was repeated a total of 50 times.

Figure 1A:
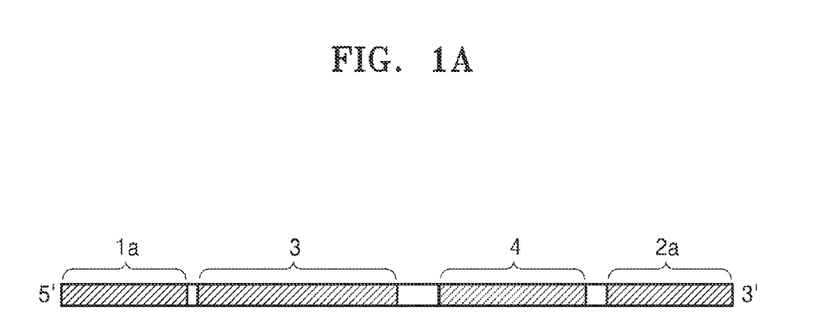
FIG. 1A is a schematic diagram of one embodiment of a polynucleotide useful for detecting a target nucleic acid, in accordance with the methods described herein.
Figure 1B:
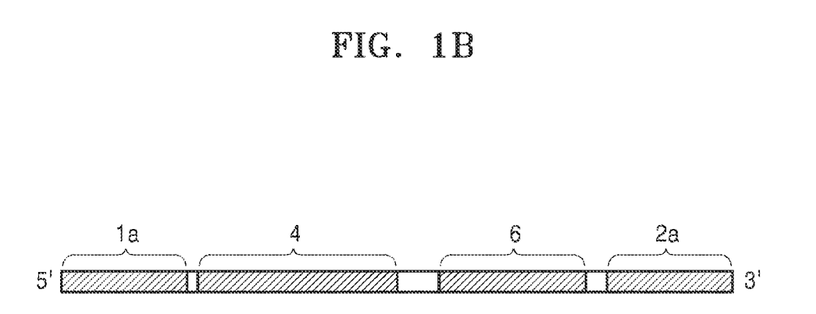
FIG. 1B is a schematic diagram of another embodiment of a polynucleotide useful for detecting a target nucleic acid, in accordance with the methods described herein.
Figure 1C:
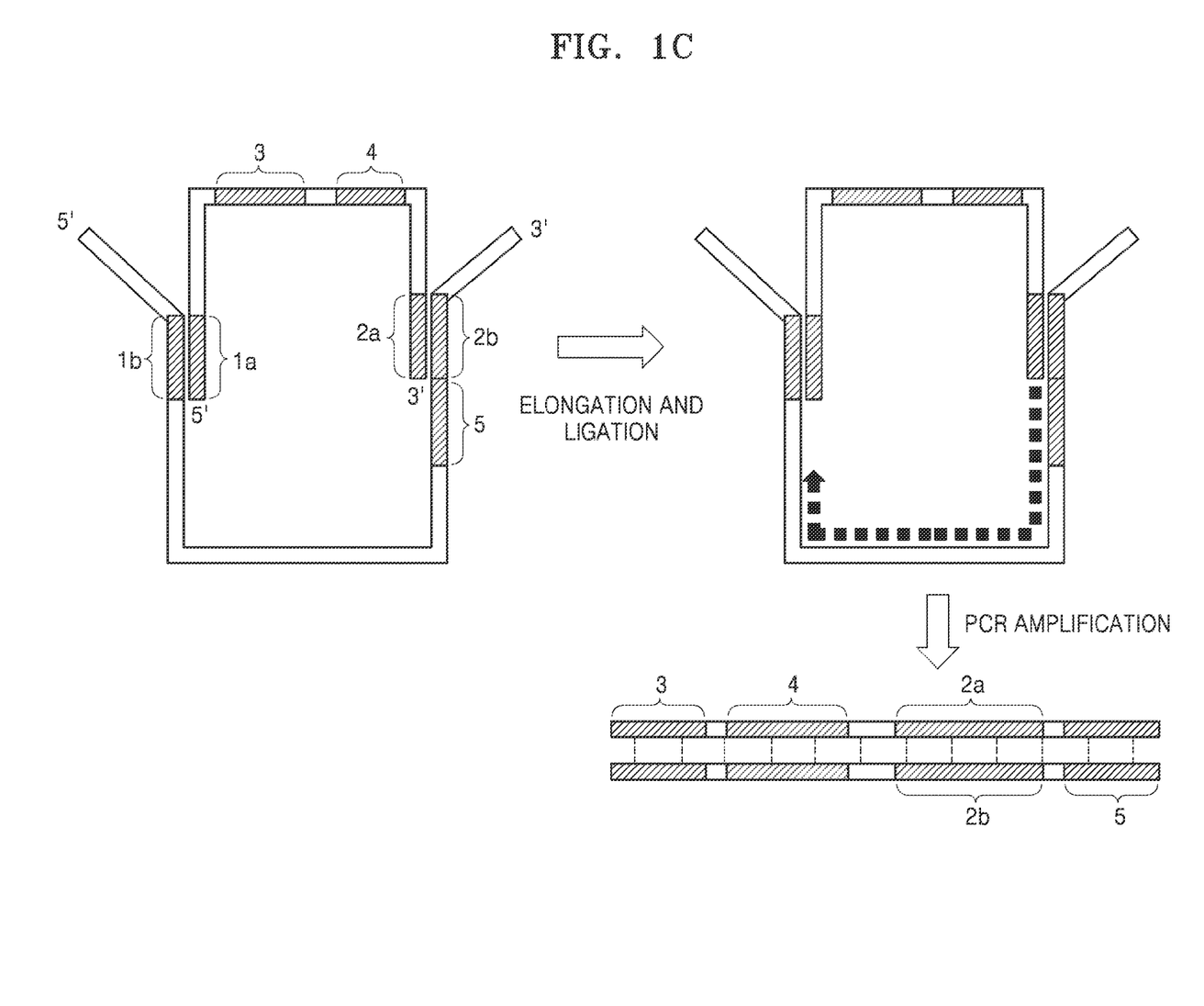
FIG. 1C is a schematic diagram illustrating a process of quantitative real-time polymerase chain reaction (qRT-PCR) using the polynucleotide of FIG. 1A.
Figure 1D:
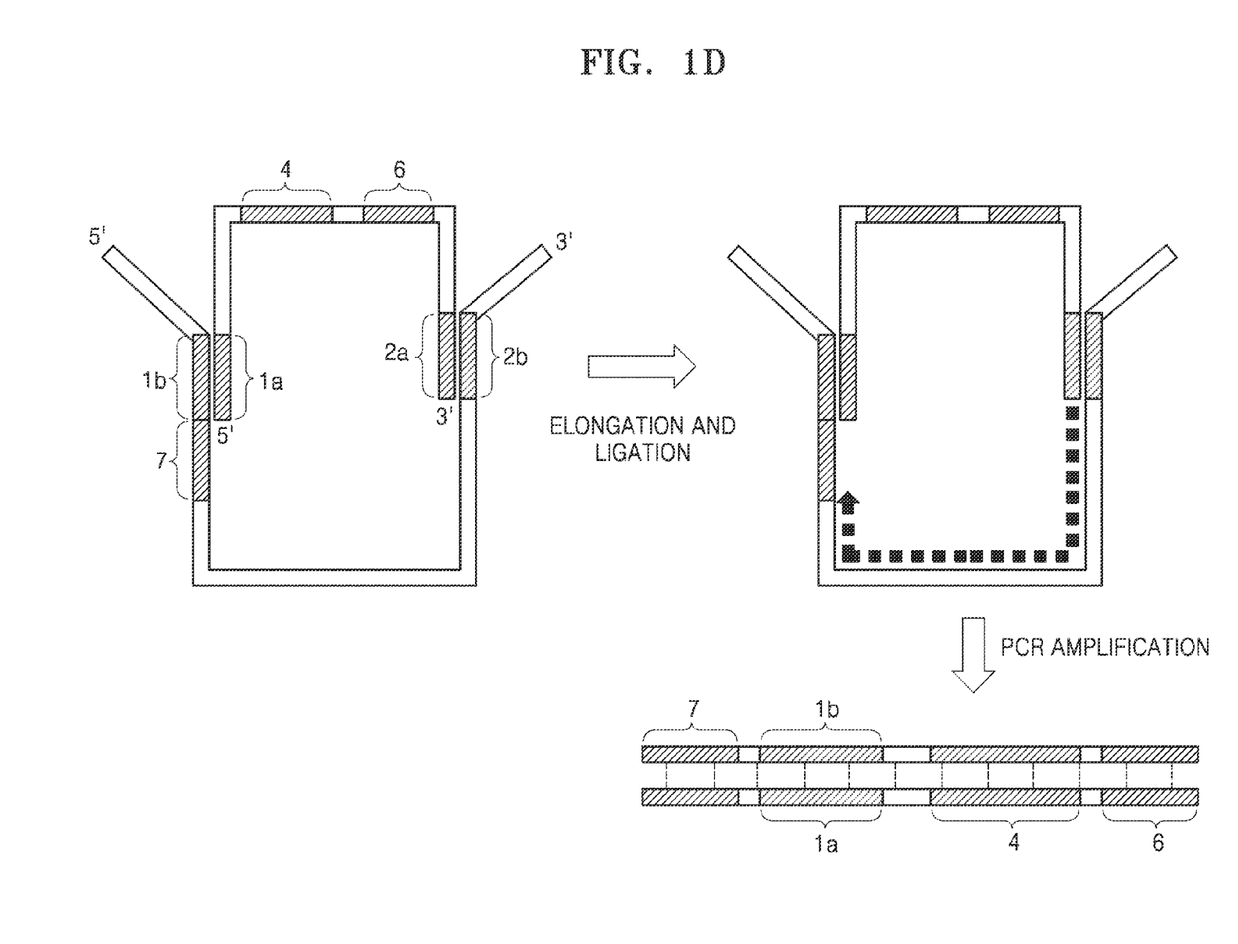
FIG. 1D is a schematic diagram illustrating a process of quantitative real-time polymerase chain reaction (qRT-PCR) using the polynucleotide of FIG. 1B.
Figure 2A:
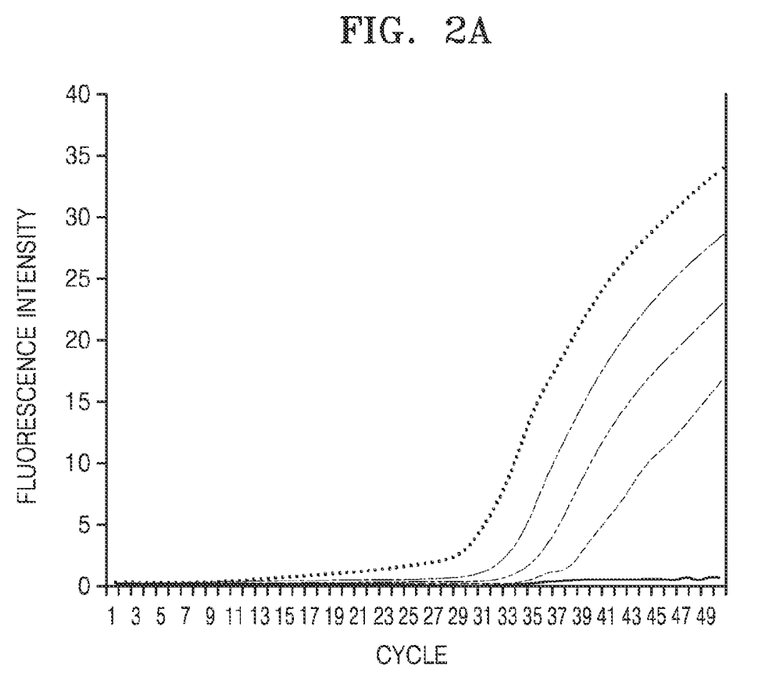
FIG. 2A is a graph displaying the relationship between a number of amplification cycles and fluorescence intensity obtained from qRT-PCR performed on human genomic DNA samples ranging in size from 8 ng to 1000 ng (x-axis: a number of amplification cycles; y-axis: fluorescence intensity (Rn))

A graph showing a relationship between a number of qRT-PCR cycles and fluorescence intensity obtained from the qRT-PCR is shown in FIG. 2A (x-axis: a number of amplification cycles; y-axis: fluorescence intensity (Rn), wherein the dotted/segmented curves correspond to the following, from highest to lowest fluorescence intensity, at cycle 39: 1000 ng of human genomic DNA, 200 ng of human genomic DNA, 40 ng of human genomic DNA, and 8 ng of human genomic DNA), and the graph was analyzed. The amount of human genomic DNA and the cycle threshold (Ct) values calculated from the graph are shown in Table 2 below and FIG. 2B (x-axis: $\log_{in}$ (amount of human genomic DNA), y-axis: Ct value, solid line: an actual linear line, dotted line: a calculated linear line) (y=−2.362x+39.47, $R^2$=0.9976).

TABLE 2

| Amount of human genomic DNA (ng) | Ct value | Coefficient of variation (CV) (%) |
|---|---|---|
| 8 | 37.2 | 0.9 |
| 40 | 34.5 | 1.0 |
| 200 | 32.4 | 0.5 |
| 1000 | 30.1 | 0.3 |

Figure 2B:
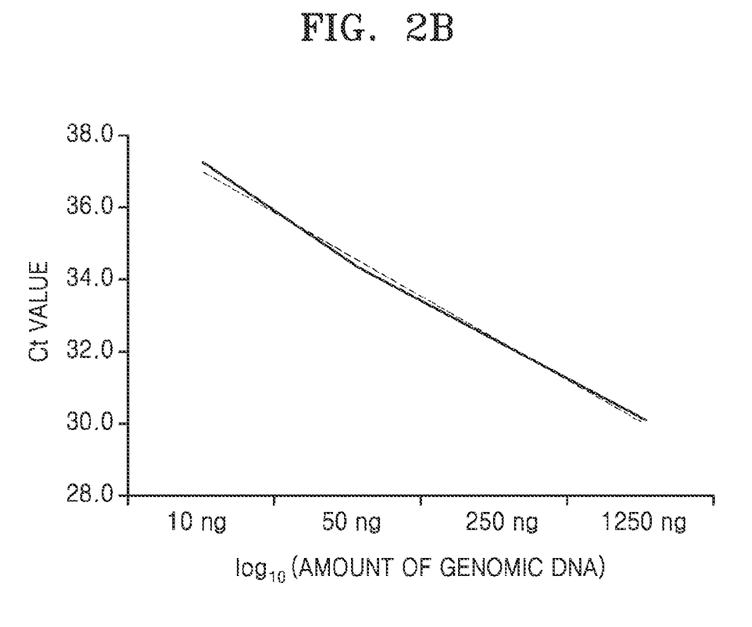
FIG. 2B is a graph displaying the relationship between $\log_{10}$ (amount of human genomic DNA) and a Ct (cycle threshold) value derived the data in FIG. 2A (x-axis: $\log_{10}$ (amount of human genomic DNA), y-axis: Ct value, solid line: an actual linear line, dotted line: a calculated linear line).

As shown in Table 2 above and FIG. 2B, the slope was shown to be about −2.36, which is similar or close to the ideal value of −2.33, when the amount of the human genomic DNA was about 8 ng to about 1000 ng.

As described above, according to the one or more of the above embodiments of the present invention, when a method of detecting a target nucleic acid, a polynucleotide and a composition used for the method are used, longer target nucleic acids may be detected and quantified with high sensitivity and precision.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting a target nucleic acid, the method comprising:

incubating a first polynucleotide and a sample comprising a target nucleic acid, whereby the target nucleic acid and the first polynucleotide hybridize to form a hybridization product, wherein the first polynucleotide comprises a first complementary region that hybridizes to a first region of the target nucleic acid; and a second complementary region that hybridizes to a second region of the target nucleic acid, wherein the second region of the target nucleic acid is located 3' of the first region on the target nucleic acid, and the first region and second region of the target nucleic acid are separated by about 18 nucleotides to about 10000 nucleotides; and the second complementary region is located 3' of the first complementary region on the first polynucleotide;

incubating the hybridization product in the presence of a first nucleic acid polymerase to extend the first polynucleotide to prepare an extended product;

incubating the extended product in the presence of a nucleic acid ligase to prepare a second polynucleotide having a cyclic structure;

incubating the second polynucleotide having a cyclic structure in the presence of a primer set and a second nucleic acid polymerase to amplify the second polynucleotide having a cyclic structure to prepare an amplification product, wherein the primer set comprises a forward primer comprising a polynucleotide sequence of 15-30 nt that are identical to continuous nucleotides of a third region of the first polynucleotide located between the first complementary region and the second complementary region of the first polynucleotide, and a reverse primer comprising a polynucleotide sequence of 15-30 nt that are identical to continuous nucleotides located between the first region and the second region of the target nucleic acid, or a forward primer comprising a polynucleotide sequence of 15-30 nt that are identical to continuous nucleotides located between the first region of the target nucleic acid and the second region of the target nucleic acid, and a reverse primer comprising a polynucleotide sequence of 15-30 nt that are identical to continuous nucleotides located between the first complementary region of the first polynucleotide and the second complementary region of the first polynucleotide; and detecting the amplification product to detect the target nucleic acid.

2. The method of claim 1, wherein the amplification of the second polynucleotide having a cyclic structure is performed in a presence of a probe, wherein the probe comprises a polynucleotide sequence that is identical or complementary to continuous nucleotides located between the first and second complementary regions of the first polynucleotide and hybridizes to the amplification product.

3. The method of claim 2, wherein the detection of the amplification product comprises hybridizing the probe and the amplification product and detecting a probe signal.

4. The method of claim 2, wherein the probe is labeled with a fluorescence resonance energy transfer (FRET) set.

5. The method of claim 3, wherein the detection of the amplification product occurs in real-time.

6. The method of claim 1, wherein the detection of the amplification product comprises detecting a zone improvement plan code (zip-code) sequence comprising a polynucleotide sequence identical or complementary to continuous nucleotides located between the first and second complementary regions of the first polynucleotide.

7. The method of claim 6, wherein the detection of the zip-code sequence comprises hybridizing the zip-code sequence and a polynucleotide having a sequence complementary to the zip-code sequence, wherein the polynucleotide is bound to a solid support.

8. The method of claim 1 further comprising quantifying the target nucleic acid.

9. The method of claim 1, wherein at least one of the first nucleic acid polymerase and the second nucleic acid polymerase is a DNA polymerase.

10. The method of claim 9, wherein the DNA polymerase is a T4 DNA polymerase, a T7 polymerase, a Klenow fragment, a DNA polymerase I, a Taq DNA polymerase, a Bst DNA polymerase (exonuclease minus), a pyrophage 3173 DNA polymerase, a Tth DNA polymerase, a Pfx DNA polymerase, a Tfi DNA polymerase, a Tfl DNA polymerase, a hot start polymerase, a BcaBEST DNA polymerase, or any combination thereof.

11. The method of claim 1, wherein the nucleic acid ligase is a DNA ligase.

12. The method of claim 11, wherein the DNA ligase is a T4 DNA ligase, a T3 DNA ligase, a T7 DNA ligase, an *Escherichia coli* DNA ligase, ssDNA ligase, or any combination thereof.

13. The method of claim 1, wherein the amplification of the second polynucleotide having a cyclic structure comprises thermal cycling amplification.

14. The method of claim 1, wherein the amplification of the second polynucleotide having a cyclic structure is performed by a polymerase chain reaction (PCR), a nucleic acid sequence-based amplification (NASBA), a ligase chain reaction (LCR), a strand displacement amplification (SDA), a multiple displacement amplification (MDA), a rolling circle amplification (RCA), or any combination thereof.

15. The method of claim 1, wherein the amplification of the second polynucleotide having a cyclic structure comprises isothermal amplification.

\* \* \* \* \*